US008283183B2

(12) United States Patent
Ikeda et al.

(10) Patent No.: US 8,283,183 B2
(45) Date of Patent: Oct. 9, 2012

(54) DETECTING METHOD, DETECTION DEVICE AND DETECTION KIT

(75) Inventors: Takashi Ikeda, Yokohama (JP); Norihiko Utsunomiya, Machida (JP); Junta Yamamichi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1891 days.

(21) Appl. No.: 11/114,077

(22) Filed: Apr. 26, 2005

(65) Prior Publication Data
US 2005/0244873 A1  Nov. 3, 2005

(30) Foreign Application Priority Data
Apr. 28, 2004  (JP) .................... 2004-132606

(51) Int. Cl.
*G01N 33/533* (2006.01)
*H01G 4/16* (2006.01)
(52) U.S. Cl. .................... 436/526; 360/324.2
(58) Field of Classification Search ............ 436/526; 360/324.2
See application file for complete search history.

(56) References Cited

U.S. PATENT DOCUMENTS

| 4,444,879 | A  | * | 4/1984 | Foster et al. | 435/7.95 |
| 6,219,275 | B1 |   | 4/2001 | Nishimura | 365/173 |
| 6,452,764 | B1 | * | 9/2002 | Abraham et al. | 360/324.2 |
| 6,468,809 | B1 | * | 10/2002 | Prinz et al. | 436/526 |
| 6,743,639 | B1 | * | 6/2004 | Tondra et al. | 436/518 |
| 7,048,890 | B2 | * | 5/2006 | Coehoorn et al. | 422/82.02 |
| 2005/0106758 | A1 |   | 5/2005 | Fukumoto et al. | 436/526 |

FOREIGN PATENT DOCUMENTS

| JP | H11-213650 | 8/1999 |
| JP | 2002-359415 | 12/2002 |
| JP | 2002-367124 | 12/2002 |
| WO | 03/054523 A | 7/2003 |
| WO | WO 03/067258 | 8/2003 |

OTHER PUBLICATIONS

Graham et al. "High sensitivity detection of molecular recognition using magnetically labelled biomolcules and amgnetoresistive sensors" Biosensors & Bioelectronics 18 (2003) 483-4899.*
Mark Tondra et al., "Model for Detection of Immobilized Superparamagnetic Nanosphere Assay Labels Using Giant Magneto-Resistive Sensors", *J. Vac. Soc. Technology A* 18(4), Jul.-Aug. 2000, pp. 1125-1129.
J. C. Rife et al., "Design and Performance of GMR Sensors for the Detection of Magnetic Microbeads in Biosensors", *Sensors and Actuators A*, 107 (2003), pp. 209-218.
Office Action dated Nov. 8, 2011, issued by JPO in counterpart Japanese patent application 2008-242567 (in Japanese, English summary of relevant portion provided above).

\* cited by examiner

*Primary Examiner* — Mark Shibuya
*Assistant Examiner* — Pensee Do
(74) *Attorney, Agent, or Firm* — Fitzpatrick, Cella, Harper & Scinto

(57) ABSTRACT

A detection device and a detecting method using the detection device are provided in which a magnetic particle is used as a marker particle, and the ratio of a region with reversed magnetization to the whole area of a free layer of a magnetoresistive effect film is increased by a stray magnetic field generated through a biochemical reaction from the magnetic particle remaining on a surface of the magnetoresistive effect film, so that a large detection signal is obtained and obtained detection data can be stored with stability.

10 Claims, 5 Drawing Sheets

DETECTING METHOD, DETECTION DEVICE AND DETECTION KIT

BACKGROUND OF THE INVENTION

1. Field of the Invention

The present invention relates to a detection device for detecting a magnetic particle in a sample solution, a detecting method and a detection kit.

2. Related Background Art

A number of techniques such as radioimmunoanalysis and enzyme antibody technique have been proposed and implemented as immunoanalysis until now. For example, in radioimmunoassay (RIA) or immunoradiometric assay (IRMA), a competitive antigen or antibody is labeled with a radionuclide, and the antigen is quantitatively measured based on measurement results of a specific activity. An advantage of this method is its high sensitivity, but a special facility or apparatus is necessary in view of the safety of radionuclides. The enzyme antibody technique using an enzyme for labeling an antibody can be handled more easily than radioimmunoanalysis and provides a practical sensitivity. However, higher sensitivity and more ease of handling are demanded.

Under these circumstances, methods for readily detecting, by using giant magnetoresistive effect (GMR) elements, a small amount of magnetic particles used as labeling substances have been proposed in recent years (for example, David R. Baselt, et al., "Biosensors & Bioelectronics 13,731" (1998)(document 1), D. L. Graham, et al., "Biosensors & Bioelectronics 18,483" (2003)(document 2)).

In document 1, GMR films of 80 μm×5 μm and 20 μm×5 μm are used and a plurality of magnetic particles with a diameter of 2.8 μm are detected. FIG. 4 shows that a stray magnetic field is applied from a magnetic particle to a GMR film. A magnetic film used for the GMR film is an in-plane magnetized film, and a magnetic field 180 is applied to the magnetic particle perpendicularly to a surface of the magnetic film. Therefore, as shown in FIG. 4, a stray magnetic field 182 generated from a magnetic particle 174 is applied to the magnetic film of a GMR film 300 almost in the in-plane direction of the film. The magnetic particle 174 has been magnetized by the application of the magnetic field. The magnetization of the magnetic film is aligned with the direction of the magnetic field. Reference numeral 181 denotes the magnetization direction of the magnetic particle.

The electrical resistance of the GMR element depends upon the relative magnetization directions of two magnetic films. Parallel magnetization has a relatively low electrical resistance. Antiparallel magnetization has a relatively high electrical resistance. In order to obtain parallel and antiparallel magnetization, the magnetization direction of one of the two magnetic films of the GMR element is fixed, and the other of the magnetic films is made of a magnetic material having a coercive force allowing a stray magnetic field from a magnetic particle to reverse magnetization. In the absence of a magnetic particle on the GMR element, even when an external magnetic field is applied, a magnetic field is not applied to the magnetic film in the in-plane direction of the film, and so magnetization is not reversed. Further, a detection circuit is configured as follows: a bridge circuit is constituted of two fixed resistors, a GMR element where a magnetic particle is not fixed, and a GMR element where a magnetic particle can be fixed. A potential difference induced by the bridge circuit is detected by a locking amplifier.

In document 2, GMR elements of 2 μm×6 μm are used and a magnetic particle having a diameter of 2 μm is detected. As in document 1, the GMR element where a magnetic particle can be fixed and the GMR element where a magnetic particle cannot be fixed are formed side by side, and the output signals of the two GMR elements are compared with each other, so that a magnetic particle is detected. A magnetic film is an in-plane magnetized film, and a magnetic field is applied to the magnetic particle in the longitudinal direction of the magnetic film in the plane of the film.

As described above, in the methods of detecting a magnetic particle by using the GMR elements, a magnetic particle is magnetized in a desired direction and the magnetization direction of a magnetoresistive effect film is changed by a stray magnetic field generated from the magnetic particle, thereby achieving ease of handling and detection in a relatively short time.

As described above, the electrical resistance of the magnetoresistive effect film is changed by the magnetization of the two magnetic films. In the magnetic film where magnetization can be reversed, when a region where magnetization is reversed is only a part of the magnetic film, the resulting magnetoresistance effect becomes smaller than that of a magnetic film where magnetization is entirely reversed. For example, when a magnetic particle has a small diameter and a magnetoresistive effect film has quite a small region of reversed magnetization, the resulting change in electrical resistance is small, and thus detection cannot be made.

Particularly in the case of a stray magnetic field of superparamagnetism, when the application of an external magnetic field to the magnetic particle is stopped, a stray magnetic field is not generated from the magnetic particle and a small magnetic domain easily disappears, which has been formed locally on the magnetic film of the magnetoresistive effect film. Thus, it becomes difficult to store information on the detected magnetic particle.

SUMMARY OF THE INVENTION

In view of these problems, the present invention proposes a device and a method thereof whereby even a single magnetic particle with a small stray field can be detected by a large signal and information on the detected magnetic particle can be stored with stability in a detection device for detecting a magnetic particle in a sample solution by using a magnetoresistive effect film.

The present invention is a detection device for detecting a magnetic particle in a sample solution, wherein a magnetoresistive effect film is used as a sensing element, the magnetoresistive effect film having a first magnetic film with a fixed magnetization direction and a second magnetic film serving as a perpendicularly magnetized film with a magnetization direction variable at the detection of a magnetic particle, and the surface of the second magnetic film is disposed on or inside a circle having a radius of $2^{1/2}d$, where d represents the distance between the surface of the second magnetic film and the center of the magnetic particle.

The present invention is a detection device for detecting a magnetic particle in a sample solution, the device comprising a magnetoresistive effect film including a first magnetic film with a fixed magnetization direction and a second magnetic film serving as an in-plane magnetized film with a magnetization direction variable at the detection of a magnetic particle, wherein the surface of the second magnetic film is disposed on or inside a circle having a radius of $d/2^{1/2}$, where d represents the distance between the surface of the second magnetic film and the center of the magnetic particle.

The present invention is a detection device for detecting a magnetic particle in a sample solution, the device comprising a magnetoresistive effect film including a first magnetic film with a fixed magnetization direction and a second magnetic film with a magnetization direction variable at the detection of a magnetic particle, wherein the second magnetic film has a single magnetic domain structure.

Other features and advantages of the present invention will be apparent from the following description taken in conjunction with the accompanying drawings, in which like reference characters designate the same or similar parts throughout the figures thereof.

Figure 1:
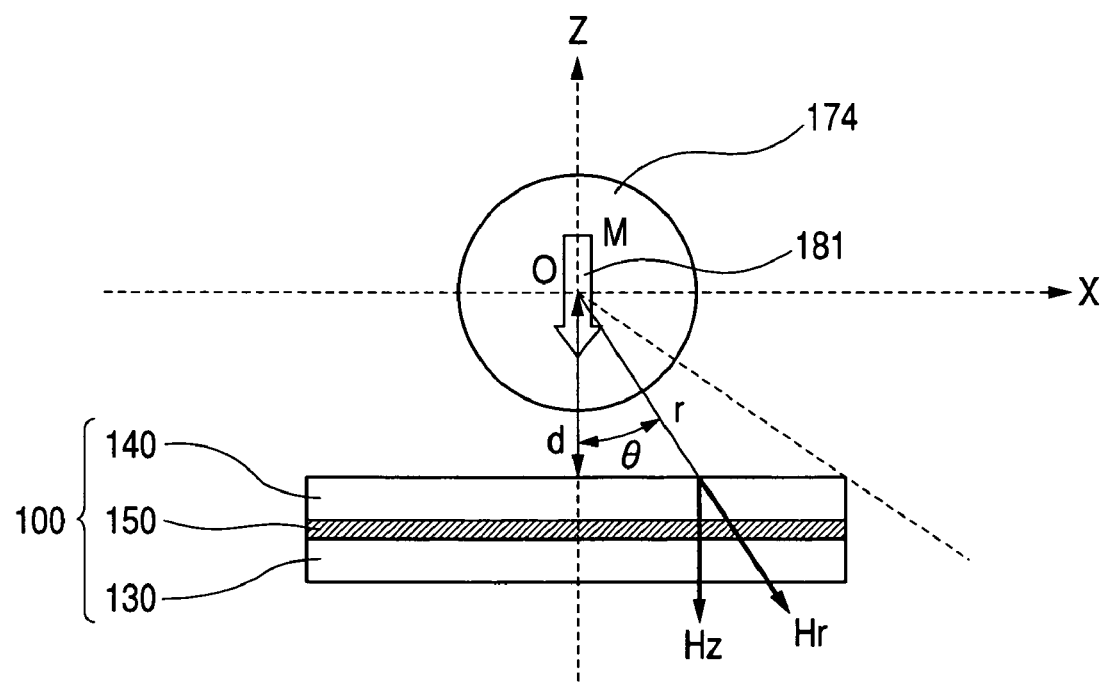
FIG. 1 is a conceptual drawing for explaining the polarity of a perpendicular component of a stray magnetic field generated from a magnetic particle when the magnetic particle is magnetized perpendicularly to a surface of a magnetoresistive effect film in a detection device of the present invention.

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

The present invention will be specifically described below. In the following example, an antigen is detected in a sample solution containing a marker substance as a magnetic particle.

A detection device is configured so that a GMR film is formed as a magnetoresistive element on a substrate. A fixation layer is formed on a surface of the GMR film and a primary antibody is fixed thereon. A magnetic film of the GMR film is a perpendicularly magnetized film. In the initial state, two magnetic films are both magnetized upward. In order to detect the electric resistance of the GMR film, electrodes are formed on the right and left ends of the GMR film or above and below the GMR film. A constant current source and a voltmeter are connected to the electrodes. To obtain a large signal at the detection of a magnetic particle, it is preferable to arrange the electrodes so as to apply current perpendicularly to a surface of the magnetoresistive element.

In this example, a GMR film is used as a magnetoresistive effect film. A tunneling magnetoresistance (TMR) film and a ballistic magnetoresistance (BMR) film may be also used. The TMR and BMR films are more preferable because of a higher magnetoresistance ratio. Both of a perpendicularly magnetized film and an in-plane magnetized film can act as a magnetic film. A well-known material can be used for the perpendicularly magnetized film. For example, an alloy or artificial lattice film of a rare-earth metal and a transition metal and an alloy or artificial lattice film of a transition metal and a precious metal are available. However, a free layer (a magnetic film where magnetization is reversed by a stray magnetic field from a magnetic particle) requires a small coercive force and thus, of rare-earth metals, gadolinium is preferably used. A pinned layer (a magnetic film where the direction of magnetization is fixed) requires a large coercive force, and thus, of rare-earth metals, terbium and dysprosium are preferably used. When an in-plane magnetized film is used, nickel with a relatively small coercive force or an alloy film of nickel and other transition metals is preferably used for the free layer. Further, iron and cobalt or an alloy film of iron and cobalt are preferably used for the pinned layer. In order to prevent the reversal of magnetization when a large magnetic field is applied, it is preferable that an antiferromagnetic film be exchange-coupled to the pinned layer. Moreover, in order to obtain a large change in magnetic resistance in a GMR film and a TMR film, it is preferable to form a magnetic material of high spin polarizability on an interface of a non-magnetic film and a magnetic film.

A sample solution is poured into a detection device, and an antigen in the sample solution is fixed to an antibody which has been fixed on the GMR film. Then, a secondary antibody in which a magnetic particle is fixed as a marker substance is put into the detection device, coupled to the antigen, and fixed on the GMR film. Thereafter, a magnetic particle having no antigen-antibody reaction is removed from the GMR film. In this process, when a target antigen is present in the sample solution, a magnetic particle is fixed on the GMR film. When no target antigen is present in the solution, magnetic particles are all removed. In this example, the secondary antibody is caused to react after the primary antibody and a specimen are caused to react. The specimen may be caused to react with the primary antibody after reacting with the secondary antibody. A conventionally used antibody is applicable to the present invention. Various antibodies can be used as the secondary antibody to be fixed to a magnetic particle. A target specimen enables specific identification of an antibody of a biological material (protein, nucleic acid and sugar chain), an allergen, a bacterium, a virus and so on.

Figure 3:
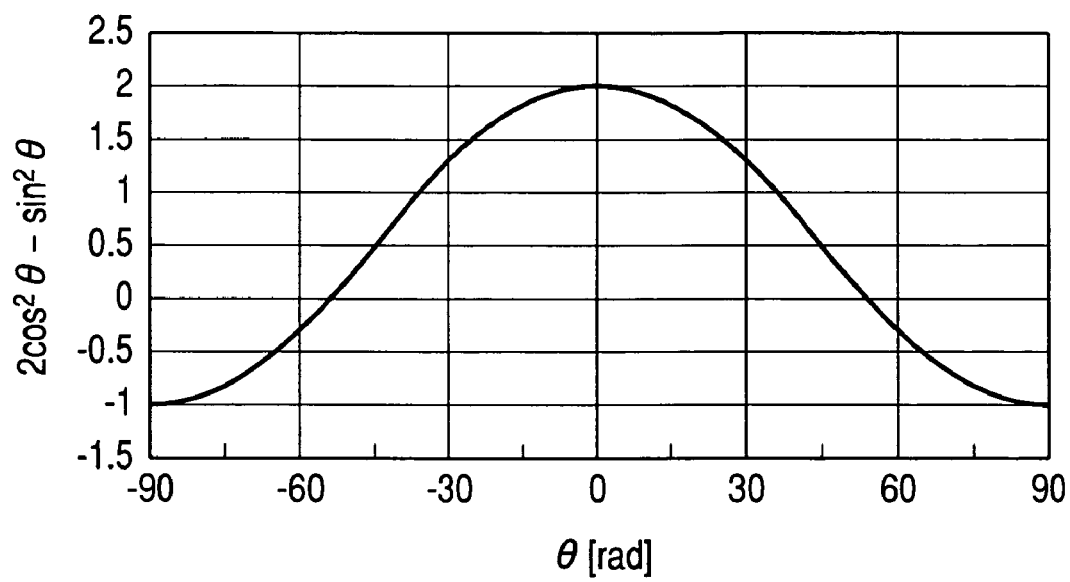
FIG. 3 is a graph for explaining the polarity of the perpendicular component or the in-plane component of the stray magnetic field generated from the magnetic particle.
Figure 4:
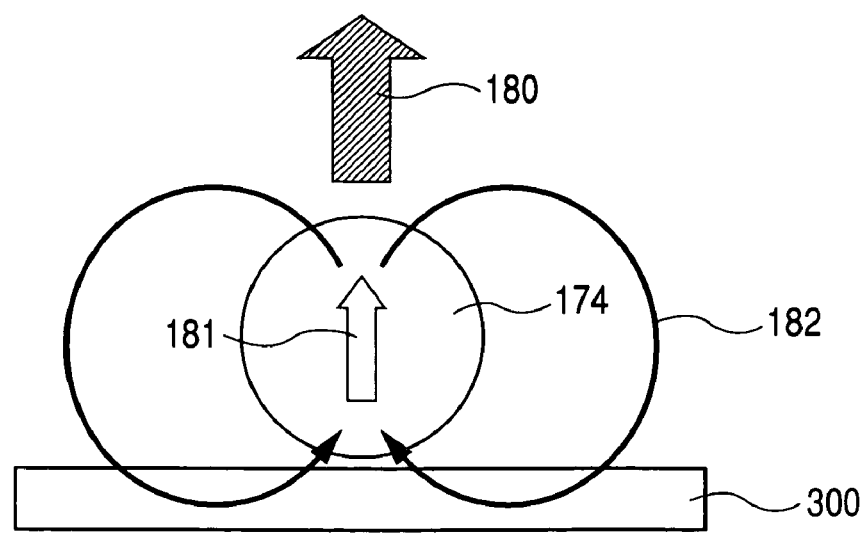
FIG. 4 is a conceptual drawing for explaining the direction of a stray magnetic field applied from a magnetic particle to a magnetoresistive effect film in a magnetic particle detection device of document 1.

Subsequently, an external magnetic field is applied downward in a perpendicular direction to a film surface to magnetize a magnetic particle. However, the size of the external magnetic field is not so large as to reverse the magnetization of the GMR film. As is generally known, when a magnetic particle is magnetized to a magnetization M, a downward component Hz of a stray magnetic field generated from the magnetic particle is expressed by the formula below (see FIG. 1):

$$H_Z = \frac{M}{4\pi\mu r^3} \cdot (2\cos^2\theta - \sin^2\theta) \quad (1)$$

where μ represents a magnetic permeability, r represents distance from the center of the magnetic particle, and θ represents an inclination from a direction perpendicular to a surface of a magnetic film. FIG. 3 shows a change in 2 cos² θ-sin² θ relative to θ. As is understood from FIG. 3, when θ is about −55 deg to 55 deg, a stray magnetic field is directed downward (2 cos² θ-sin² θ is a positive value), whereas when θ is about −55 deg to −90 deg and 55 deg to 90 deg, the stray magnetic field is directed upward. That is, due to the presence of the magnetic particle, a region where magnetization can be reversed is limited to the range of −55 deg to 55 deg. For example, a magnetic particle is present on a magnetoresistive effect film which is sufficiently large relative to the diameter of the magnetic particle, and a stray magnetic field from the magnetic particle is applied to the magnetoresistive effect film. In this case, the region with reversed magnetization is small relative to the whole area of the magnetic film, resulting in a small change in the resistance of the magnetoresistive effect film. When the region with reversed magnetization is small, the magnetic domain easily disappears, which is formed in the magnetic film to reduce domain wall energy. Thus, it is not possible to store the detection result of the magnetic particle, that is, an antigen.

Hence, the size of the free layer is set within a region where a stray magnetic field from a magnetic particle is applied in a positive direction, that is, within a circle having a radius of $2^{1/2}d$, where d represents the distance between a surface of the free layer and the center of the magnetic particle, so that the ratio of the area with reversed magnetization to the area of the free layer is increased and a sufficiently large signal can be obtained even with a single magnetic particle. Since the ratio of the area with reversed magnetization to the area of the free layer is large, a formed magnetic domain is stored as it is or is expanded to reverse the magnetization of the entire free layer, so that the obtained detection result of an antigen can be stored with stability.

In the above description, the perpendicularly magnetized film is used as the magnetic film of the magnetoresistive effect film. In the following case, an in-plane magnetized film is used.

Figure 2:
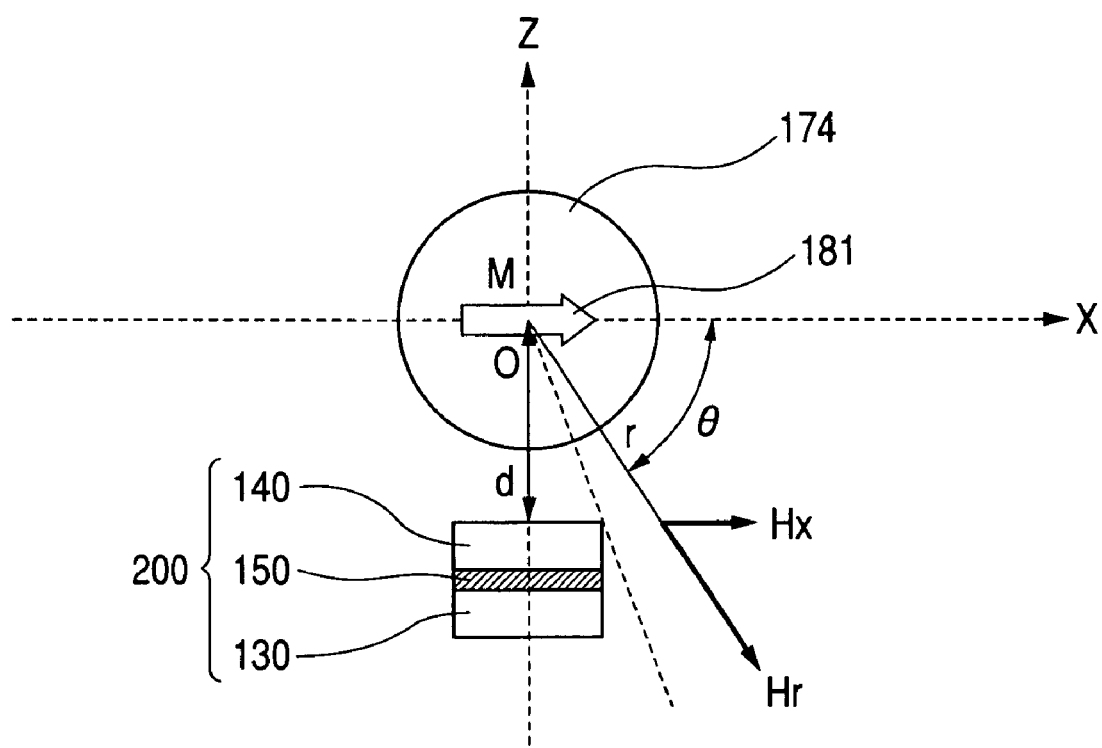
FIG. 2 is a conceptual drawing for explaining the polarity of an in-plane component of a stray magnetic field generated from a magnetic particle when the magnetic particle is magnetized in the in-plane direction of a magnetoresistive effect film in the detection device of the present invention.

As shown in FIG. 2, a magnetic particle is magnetized rightward and the in-plane magnetized film is positioned below the magnetic particle. A free layer is magnetized rightward in the initial state as the magnetic particle is magnetized. Like formula 1, on a point at a distance r from the central point of the magnetic particle, an in-plane component $H_X$ of a stray magnetic field is expressed by the formula below:

$$H_X = \frac{M}{4\pi\mu r^3} \cdot (2\cos^2\theta - \sin^2\theta) \qquad (2)$$

where θ in formula (2) is independent of θ in formula (1).

Therefore, when θ in formula (2) is about 55 deg to 125 deg, the stray magnetic field from the magnetic particle is so directed as to reverse the magnetization of the free layer, that is, the stray magnetic field is directed to the left relative to the magnetoresistive effect film. In other words, when a distance is d from the center of the magnetic particle to the surface of the free layer, the size of the free layer is set within a circle having a radius of $d/2^{1/2}$, so that the ratio of the area with reversed magnetization to the area of the free layer is increased, and a sufficiently large signal can be obtained even with a single magnetic particle. Since the ratio of the area with reversed magnetization to the area of the free layer is large, a formed magnetic domain is stored as it is or expanded to reverse the magnetization of the entire free layer, so that the obtained detection result of an antigen can be stored with stability.

The size of the free layer is limited thus, so that the ratio of the area with reversed magnetization to the area of the free layer is increased, the detection signal can be increased, or a detection result can be stored. A large detection signal can be obtained also by a free layer composed of a magnetic substance having a single magnetic domain structure. To be specific, when the magnetization of the free layer is partially reversed by a stray magnetic field generated from a magnetic particle, a magnetic substance having a single magnetic domain structure reverses the magnetization of a region where no magnetic field for reversing magnetization is applied, so that no domain wall is formed inside the magnetic substance. In the end, magnetization is reversed in the entire region of the free layer.

Embodiment 1

Figure 5:
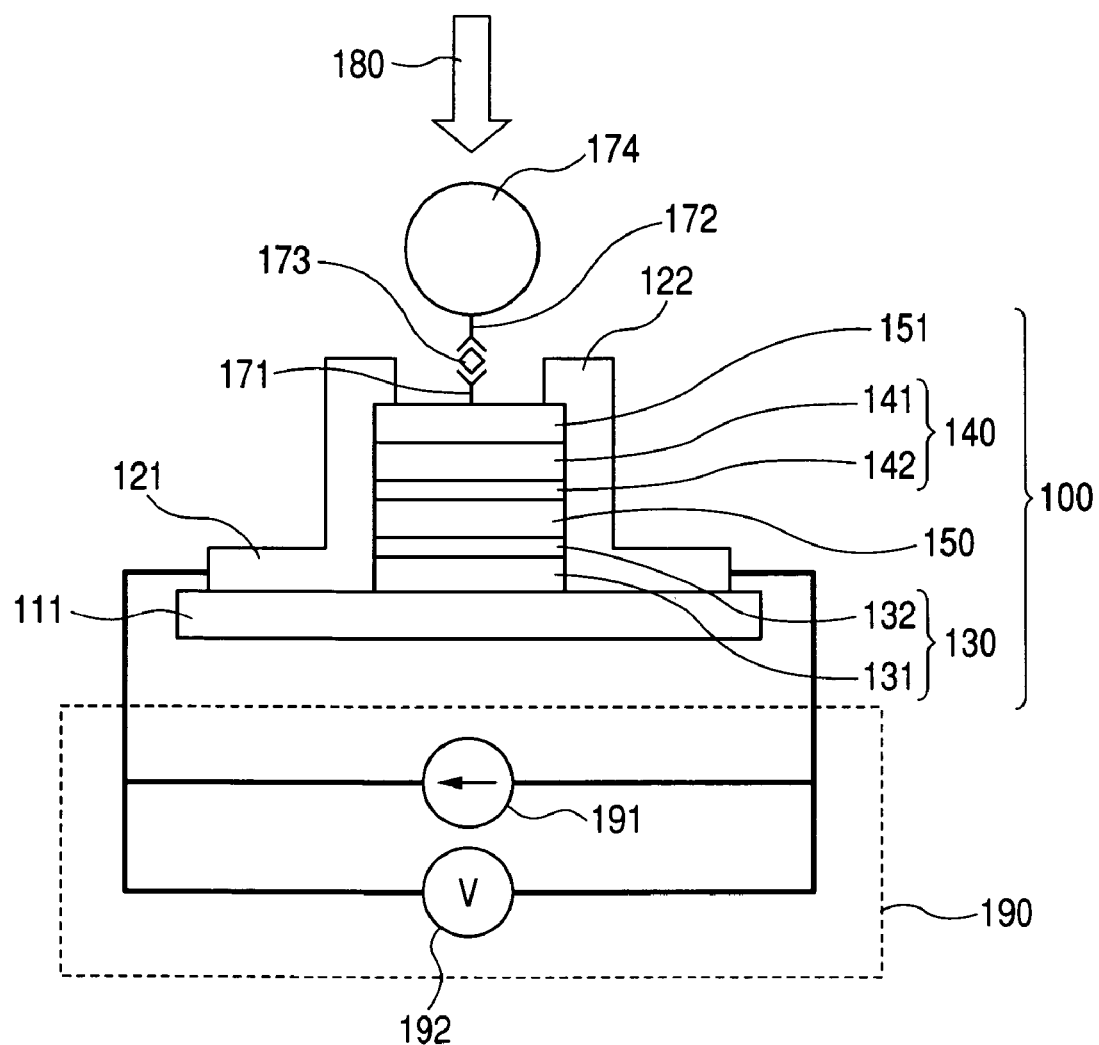
FIG. 5 is a conceptual drawing showing a detection device according to Embodiment 1 of the present invention.

FIG. 5 is a schematic diagram which shows the cross-section of a detection device for the description of the first preferred embodiment of the present invention. On a substrate 111, a magnetoresistive effect film 100 is formed in which a first perpendicularly magnetized film 131, a first high spin polarizability layer 132, a nonmagnetic film 150, a second high spin polarizability layer 142, and a second perpendicularly magnetized film 141 are formed, in this order. A bilayer exchange coupling layer composed of the first perpendicularly magnetized film 131 and the first high spin polarizability layer 132 is a pinned layer 130 where a direction perpendicular to a film surface is an axis of easy magnetization and the magnetization direction is fixed. Thus, the first perpendicularly magnetized film 131 is formed of an alloy film made of terbium, iron and cobalt with a thickness of 30 nm. The composition of terbium is 21 at % which is close to a compensated composition. The first high spin polarizability layer 132 and the second high spin polarizability layer 142 are alloy films which are made of iron and cobalt with an average thickness of about 0.5 nm. The composition of Co is 40 at %. A bilayer exchange coupling film of the second perpendicularly magnetized film 141 and the second high spin polarizability layer 142 is a free layer 140 where it is necessary to reduce a coercive force to reverse magnetization with a relatively small magnetic field. Thus, the second perpendicularly magnetized film 141 is formed of an alloy consisting of gadolinium, iron and cobalt. Gadolinium forms a perpendicularly magnetized film. Any composition can be used as long as a coercive force enables the stray magnetic field of a magnetic particle to reverse magnetization. In this embodiment, gadolinium is set at 20 at %. The high spin polarizability layers 132 and 142 are in-plane magnetized films. The high spin polarizability layers 132 and 142 are reduced in thickness, so that a direction perpendicular to a film surface becomes an axis of easy magnetization in the pinned layer 130 and the free layer 140 due to exchange force with the perpendicularly magnetized film 131 or 141. The high spin polarizability layer may be shaped like an island or a network instead of a film because of a small average thickness. Also in this case, a magnetoresistance effect is enhanced. The nonmagnetic film between the free layer 140 and the pinned layer 130 is made of copper with a thickness of 3 nm. A surface of the second perpendicularly magnetized film 141 is covered with a protective film 151 which is made of silicon with a thickness of 10 nm. The size of the GMR film 100 is set within a circle having a radius of $2^{1/2}d$, where d represents the distance between the center of a magnetic particle and a surface of the magnetoresistive effect film. Electrodes 121 and 122 made of Pt are formed on both ends of the GMR film 100. In order to align the magnetization direction of the GMR film 100 with an upward direction, magnetic field applying means (not shown) is provided which applies an external magnetic field of 30 kOe to the GMR film 100 in the upward direction of a film surface. However, the coercive force of the pinned layer 130 and the free layer 140 is smaller than 30 kOe.

In order to carry a primary antibody 171 on a surface of the protective film 151, hydrophilization is first performed on the surface of the protective film 151, and then the surface is treated with an amino-silane coupling agent. Further, by using a cross-linker such as glutaraldehyde for immobilizing the primary antibody 171, a peptide chain and an amino group derived from the amino-silane coupling agent are chemically bonded to each other to fix the primary antibody 171 for complementing a desired antigen.

With this detection device, a prostate-specific antigen (PSA) known as a marker of a prostate cancer can be detected according to the protocol below. The primary antibody 171 for identifying a PSA is fixed in the detection device.

(1) The device is dipped into phosphate buffered saline (sample solution) containing a PSA which is the antigen (sample) 173, and incubation is carried out for five minutes.
(2) The unreacted PSA is cleaned with phosphate buffered saline.
(3) After steps (1) and (2), the device is dipped into phosphate buffered saline containing an anti-PSA antibody (secondary antibody) which is labeled by a magnetic particle 174, and incubation is carried out for five minutes.
(4) The unreacted and labeled antibody is cleaned with phosphate buffered saline.

However, the average diameter of the magnetic particle 174 is about 400 nm and superparamagnetism is observed. It is preferable that magnetic particles do not agglomerate in the solution. Thus, it is more preferable that magnetic particles be superparamagnetic. Also in the case of a reaction on a magnetoresistive element, superparamagnetism is preferable because reaction efficiency is increased.

An average distance from a surface of the free layer 140 to the magnetic particle 174 is about 35 nm. The GMR film is equal in size to a circle having a radius of about 300 nm (on the circumference) or included in the circle.

First, constant current is applied to the GMR film 100 with no magnetic field and the voltage of the GMR film 100 is measured at that time. Then, an external magnetic field 180 of 15 Oe is applied downward to the magnetic particle 174 having been fixed on a surface of the GMR film 100 through an antigen-antibody reaction, and the magnetization of the magnetic particle 174 is directed downward. A stray magnetic field is generated from the magnetic particle 174, a combined magnetic field of the external magnetic field 180 and the stray magnetic field is applied to the free layer 140, and thus magnetization is reversed. In this state, constant current is applied to the GMR film 100 again and a change in voltage is measured, so that the antigen 173 in the sample solution can be detected.

Embodiment 2

Figure 6:
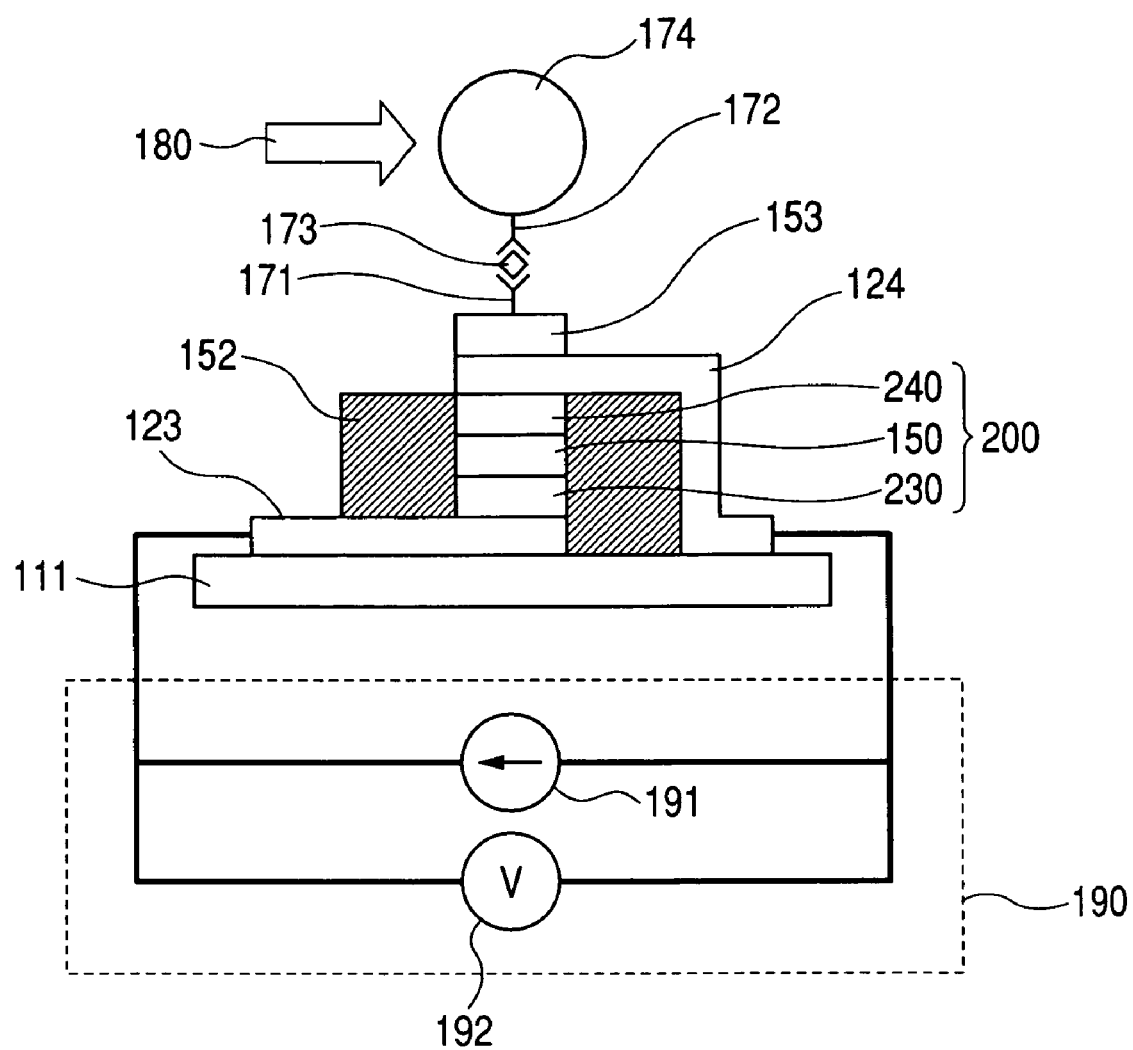
FIG. 6 is a conceptual drawing showing a detection device according to Embodiment 2 of the present invention.

FIG. 6 is a schematic diagram which shows the cross-section of a detection device for the description of a second preferred embodiment of the present invention. A platinum film having a thickness of 10 nm is formed as a lower electrode 123 on a substrate 111, and a pinned layer 230 made of iron and cobalt with a thickness of 10 nm and an aluminum film with a thickness of 1.6 nm are formed thereon. A surface of the aluminum film is exposed to an atmosphere of oxygen, so that the aluminum film is formed into an alumina tunnel barrier film 150. Then, a permalloy film is formed with a thickness of 20 nm on a surface of the alumina tunnel barrier film 150 to form a free layer 240, so that a TMR film 200 is formed. Further, a platinum upper electrode 124 is formed with a thickness of 10 nm. In order to prevent an electrical short circuit on the upper electrode 124 and the lower electrode 123, an aluminum interlayer insulating film 152 is formed around the TMR film. A silicon film having a thickness of 10 nm is formed on the upper part of the free layer 240 on the platinum upper electrode 124. In order to align the magnetization direction of the TMR film 200 with a rightward direction, magnetic field applying means (not shown) is provided which applies an external magnetic field of 5 kOe to the TMR film 200 in the rightward direction.

Thereafter, as in Embodiment 1, a magnetic particle 174 is fixed on a surface of a TMR film 200 through an antigen-antibody reaction. The average diameter of the magnetic particle 174 is about 400 nm and superparamagnetism is observed. A distance from a surface of the free layer 240 to the magnetic particle 174 is 55 nm. The TMR film is a rectangle having a short side of 90 nm and a long side of 180 nm. The free layer 240 and the pinned layer 230 have a single magnetic domain structure. The longitudinal direction of a magnetic film is an axis of easy magnetization.

First, constant current is applied to the TMR film 200 in a direction perpendicular to a film surface with no magnetic field and the voltage of the TMR film 200 is measured at that time. Then, an external magnetic field 180 is applied rightward to the magnetic particle 174 which has been fixed on a surface of the TMR film 200 through an antigen-antibody reaction, and the magnetization of the magnetic particle 174 is directed rightward. A stray magnetic field is generated from the magnetic particle 174, a stray magnetic field in the opposite direction from an external magnetic field 180 (the magnetization direction of the magnetic particle 174) is applied to the free layer 240, and thus magnetization is reversed. In this state, constant current is applied to the TMR film 200 again and a change in voltage is measured, so that an antigen 173 in a sample solution is detected.

The embodiments of the present invention describe the method of detecting an antigen by means of a single magnetoresistive effect film. For example, as is disclosed in document 1, first, two magnetoresistive effect films and two fixed resistors constitute a bridge circuit. An antigen or the like may be detected as follows: a magnetic particle can be fixed on one of the magnetoresistive effect films but cannot be fixed on the other, so that a change in the resistance of the magnetoresistive effect film is detected.

Further, a number of magnetoresistive effect films are formed on a substrate and different antibodies are fixed on the surfaces of the films, so that target materials including two or more kinds of antigens can be quantitatively detected at a time.

The detecting method and the detection device described in the embodiments of the present invention are used particularly for a method of detecting a biological material. The present invention is used as a detection device which can obtain a high detection signal even with a small magnetic particle or a magnetic particle of low magnetization and stably store detection data.

This application claims priority from Japanese Patent Application No. 2004-132606 filed on Apr. 28, 2004, which is hereby incorporated by reference herein.

What is claimed is:

1. A detection device for detecting a magnetic particle in a sample solution, the device comprising:
    a magnetoresistive effect film including a first magnetic film with a fixed magnetization direction and a second magnetic film serving as a perpendicularly magnetized film with a magnetization direction variable at the detection of the magnetic particle; and
    a fixation layer for fixing the magnetic particle arranged on a surface of the second magnetic film,
    wherein all of the surface of the second magnetic film is set within a circle having a radius of $2^{1/2}d$, where d represents a distance between the surface of the second magnetic film and a center of the magnetic particle, when the magnetic particle is fixed to the magnetoresistive effect film through the fixation layer, a direction of an external magnetic field for magnetizing the magnetic particle is parallel to a magnetization direction of the second magnetic film, and all of the second magnetic film is arranged in a region in which a stray magnetic field in the same direction as the external magnetic field is applied.

2. The detection device according to claim 1, further comprising a current source to supply current to the magnetoresistive effect film, means of reading voltage of the magnetoresistive effect film, and means of applying a magnetic field to the magnetoresistive effect film.

3. The detection device according to claim 1, wherein the magnetoresistive effect film is a tunneling magnetoresistance film.

4. A detection device for detecting a magnetic particle in a sample solution, the device comprising:

a magnetoresistive effect film including a first magnetic film with a fixed magnetization direction and a second magnetic film serving as an in-plane magnetized film with a magnetization direction variable at the detection of the magnetic particle; and a fixation layer for fixing the magnetic particle arranged on a surface of the second magnetic film, wherein all of the surface of the second magnetic film is set within a circle having a radius of $d/2^{1/2}$, where d represents a distance between the surface of the second magnetic film and a center of the magnetic particle, when the magnetic particle is fixed to the magnetoresistive effect film through the fixation layer, a direction of an external magnetic field for magnetizing the magnetic particle is parallel to a magnetization direction of the second magnetic film, and all of the second magnetic film is arranged in a region in which a stray magnetic field in an opposite direction from that in which the external magnetic field is applied.

5. The detection device according to claim 4, wherein a fixation layer for fixing the magnetic particle is formed near the magnetoresistive effect film.

6. The detection device according to claim 5, further comprising a current source to supply current to the magnetoresistive effect film, means of reading voltage of the magnetoresistive effect film, and means of applying a magnetic field to the magnetoresistive effect film.

7. The detection device according to claim 4, further comprising a current source to supply current to the magnetoresistive effect film, means of reading voltage of the magnetoresistive effect film, and means of applying a magnetic field to the magnetoresistive effect film.

8. The detection device according to claim 4, wherein the magnetoresistive effect film is a tunneling magnetoresistance film.

9. A detection kit for detecting a target material in a specimen, the kit comprising at least:

a sensing element including a magnetoresistive effect film having a first magnetic film with a fixed magnetization direction and a second magnetic film serving as a perpendicularly magnetized film with a magnetization direction variable at the detection of the magnetic particle;

a fixation layer for fixing the magnetic particle arranged on a surface of the second magnetic film;

a detection reagent including a magnetic particle on which a trap for trapping the target material is fixed, wherein all of the surface of the second magnetic film is set within a circle having a radius of $2^{1/2}d$, where d represents a distance between the surface of the second magnetic film and a center of the magnetic particle, when the magnetic particle is fixed to the magnetoresistive effect film through the fixation layer, a direction of an external magnetic field for magnetizing the magnetic particle is parallel to a magnetization direction of the second magnetic film, and all of the second magnetic film is arranged in a region in which a stray magnetic field in the same direction as the external magnetic field is applied.

10. A detection kit for detecting a target material in a specimen, the kit comprising at least:

a sensing element including a magnetoresistive effect film having a first magnetic film with a fixed magnetization direction and a second magnetic film serving as an in-plane magnetized film with a magnetization direction variable at the detection of the magnetic particle;

a fixation layer for fixing the magnetic particle arranged on a surface of the second magnetic film; and a detection reagent including a magnetic particle on which a trap for trapping the target material is fixed, wherein all of the surface of the second magnetic film is set within a circle having a radius of $d/2^{1/2}$, where d represents a distance between the surface of the second magnetic film and a center of the magnetic particle, when the magnetic particle is fixed to the magnetoresistive effect film through the fixation layer, a direction of an external magnetic field for magnetizing the magnetic particle is parallel to a magnetization direction of the second magnetic film, and all of the second magnetic film is arranged in a region in which a stray magnetic field in an opposite direction from that in which the external magnetic field is applied.

* * * * *